United States Patent [19]

Stammann et al.

[11] Patent Number: 4,714,689

[45] Date of Patent: Dec. 22, 1987

[54] PROCESS FOR THE REGENERATION OF CATALYSTS FOR THE GAS-PHASE REDUCTION OF AROMATIC NITRO COMPOUNDS

[75] Inventors: Günter Stammann, Cologne; Zoltan Kricsfalussy; Helmut Waldmann, both of Leverkusen; Joachim Schneider; Harald Medem, both of Krefeld, all of Fed. Rep. of Germany

[73] Assignee: Bayer Aktiengesellschaft, Leverkusen, Fed. Rep. of Germany

[21] Appl. No.: 894,581

[22] Filed: Aug. 7, 1986

[30] Foreign Application Priority Data

Aug. 29, 1985 [DE] Fed. Rep. of Germany ....... 3530820

[51] Int. Cl.$^4$ .................. B01J 23/96; B01J 23/94; B01J 38/16; C07C 45/11
[52] U.S. Cl. ..................... 502/54; 260/689; 502/38; 502/51; 502/52; 564/420; 564/421; 564/422; 564/423
[58] Field of Search ............ 502/34, 38, 51, 52, 502/54, 515, 517; 564/420–423; 260/689

[56] References Cited

U.S. PATENT DOCUMENTS

| | | | |
|---|---|---|---|
| 2,292,879 | 8/1942 | Kise | 564/422 |
| 2,822,397 | 2/1958 | Winstrom | 564/422 |
| 2,891,094 | 6/1959 | Karkalits, Jr. et al. | 502/244 |
| 4,164,481 | 8/1979 | Ma et al. | 260/689 |

FOREIGN PATENT DOCUMENTS

| | | | |
|---|---|---|---|
| 237376 | 12/1959 | Australia | 564/422 |
| 2459761 | 7/1976 | Fed. Rep. of Germany | |
| 337348 | 10/1930 | United Kingdom | 502/34 |

OTHER PUBLICATIONS

Kirk–Othmer, Encyclopedia of Chemical Technology, 3rd edition, vol. 5, p. 21 (1979).
Ullmanns Encyclopadie der Technischen Chemie (Ullman's Encyclopaedia of Industrial Chemistry), 4th edition, vol. 13, p. 565 (1977).
L. F. Albright, F. H. Van Munster and J. C. Forman, Chem. Eng., 251–259 (1967).
A. Schulz–Walz, D. C. Hempel, Z. Kricsfalussy and C. Rasp, Chem. Ing. Technik, 53, (8), 637–640 (1981).

Primary Examiner—Paul E. Konopka
Attorney, Agent, or Firm—Sprung Horn Kramer & Woods

[57] ABSTRACT

Catalysts for the gas-phase reduction of aromatic nitro compounds to aromatic amines are regenerated by treatment of the catalyst, at elevated temperature, with a gas mixture which contains oxygen, inorganic and/or organic amines and/or nitrogen oxides and, where appropiate, steam.

16 Claims, No Drawings

1

PROCESS FOR THE REGENERATION OF CATALYSTS FOR THE GAS-PHASE REDUCTION OF AROMATIC NITRO COMPOUNDS

BACKGROUND OF THE INVENTION

The present invention relates to an improved process for the regeneration of catalysts for the gas-phase reduction of aromatic nitro compounds to aromatic amines.

The most important processes for the industrial preparation of aromatic amines are reductions of the corresponding nitro compounds in the gas phase. For example, aniline, an intermediate for rubber chemicals and for methyenediphenyl diisocyanate (precursor for polyurethanes), is produced in large quantities mainly by reduction of nitrobenzene with hydrogen in the gas phase. According to a newer process, it is also possible to prepare aniline by reduction of nitrobenzene with natural gas in the presence of catalysts containing copper chromite, and steam (see, for example, EP-OS (European Published Specification) No. 0,087,690).

With such reductions in the gas phase, the Catalyst loses activity over the course of time, that is to say there is a gradual reduction in the conversion of nitro compound, frequently associated with a decrease in selectivity. Although the catalysts used industrially can be regenerated, the intervals between regenerations then become, of necessity, increasingly short. There are reports on regeneration and the possibility of regeneration in, for example, Kirk-Othmer, Encyclopedia of Chemical Technology, 3rd edition, Volume 5, page 21 (1979) and in Ullmanns Encyclopädie der technischen Chemie (Ullmann's Encyclopaedia of Industrial Chemistry), 4th edition, Volume 13, page 565 (1977). Treatment with air (see, for example, U.S. Pat. No. 2,891,094) or with air/-stream mixtures (see, for example, U.S. Pat. No. 2,292,879), followed by a reducing after-treatment, is customary for the regeneration of catalysts for the reduction of nitrobenzene. Treatment with air/stream mixtures is indicated for the abovementioned reduction process using natural gas.

Interruptions in the production of amine caused by catalyst regeneration not only adversely affect the economics, but also represent a serious interruption in the distillation stages on continuous working up of the mixture which is obtained after the reduction. Similar problems result with the supply of hydrogen, which is frequently effected continuously by steam reforming. It is then necessary during the regenerating phase to combust the hydrogen which has been made available but not used, or to deliver it at the caloric value, since temporary shut-down of the reformer is not possible, on the contrary, operation must continue at a reduced capacity (about 40% of the full load). Thus it would be possible to improve the economics of such reduction processes for the preparation of aromatic amines if it were possible to increase the lives of the catalysts.

SUMMARY OF THE INVENTION

A process for the regeneration of catalysts for the gas-phase reduction of aromatic nitro compounds to aromatic amines has now been found, which is characterized in that the catalyst is treated, at elevated temperature, with a gas mixture which contains (a) oxygen, (b) nitrogen compounds in the form of inorganic and/or organic amines and/or nitrogen oxides and, where appropriate, (c) steam.

The regeneration process according to the invention can be employed quite generally for catalysts which have been used for the reduction of any desired aromatic nitro compounds to the corresponding aromatic amines in the gas phase. The amines which are prepared in this may be carbocyclic or heterocyclic aromatic amines and have, including the possible substituents, molecular weights up to, for example, 200. The regeneration process according to the invention is preferably employed for catalysts which have been used for the preparation of 1,3-diaminobenzene, pure toluidine isomers, mixtures of toluidine isomers and/or aniline from the corresponding nitro compounds, particularly preferably for catalysts which have been used for the preparation of aniline from nitrobenzene.

The catalysts for which the regeneration process according to the invention can be employed may have been used in a fixed bed, in a moving bed or in a fluidized bed. Accordingly, the regeneration process according to the invention can also be carried out as a fixed bed, moving bed or fluidized bed process. The regeneration process according to the invention is preferably employed for catalysts which have been used in a fixed bed, and it is likewise preferably carried out in a fixed bed. The regeneration process according to the invention is particularly preferably employed for fixed bed catalysts which have been ised in tube reactors or in tube bundle reactors.

DETAILED DESCRIPTION OF THE INVENTION

According to the invention, the particular catalysts are brought into contact with gas mixtures containing (a) oxygen, (b) nitrogen compounds in the form of inorganic and/or organic amines and/or nitrogen oxides and, where appropriate, (c) steam. It is possible in each case to use only one nitrogen compound or any desired mixture of such nitrogen compounds for this.

Catalysts which can be regenerated by the process according to the invention are those which have been used as reducing catalysts for the reduction of aromatic nitro compounds to aromatic amines in the gas phase, the reduction having been carried out with, for example, hydrogen or natural gas. The catalysts may contain, for example, the elements copper, iron, nickel, palladium and/or platinum, in metallic form or in the form of compounds, and be, where appropriate, modified by other metals or metal compounds, in particular by metal oxides. The metals, for example copper and nickel, can also be in the form of mixed oxides, in particular as chromites. One example of this is copper chromite. The catalytically active compounds can be present in a very wide variety of shapes and particle sizes, and they can be present in the form of supported catalysts. For example, they may be in the form of so-called coated catalysts on aluminium oxide supports.

Catalysts known for the gas-phase reduction of nitroaromatics to aromatic amines, which can be subjected to the process according to the invention, are described in, for example, L. F. Albright, F. H. v. Munster, J. C. Forman, Chem. Eng., Nov. 6 (1967) pages 251–259, DE-OS (German Published Specification) Nos. 2,250,844, 2,024,282, U.S. Pat. No. 2,891,094, DE-OS (German Published Specification) Nos. 2,135,155, 2,135,154, 2,214,056, and 2,244,401 and EP-OS (European Published Specification) No. 0,011,090 (corresponds to U.S. Pat. No. 4,265,834).

In a more recent process (see EP-OS (European Published Specification) No. 087,690), aniline is prepared in the gas phase by reduction of nitrobenzene with natural gas in the presence of steam and copper chromite catalysts. The regeneration according to the invention is especially suitable for this process.

The process according to the invention is preferably employed for catalysts which contain palladium and/or copper in metallic form and/or in the form of compounds. The regeneration process according to the invention is particularly preferably employed for catalysts which have been used in the preparation process according to EP-OS (European Published Specification) Nos. 0,011,090 and 0,087,690.

The gas mixture to be used according to the invention for catalyst regeneration can contain, for example, per liter of bulk volume of the particular catalyst, 5 to 100 l/h (liter at STP) of oxygen, 2 to 1,000 g/h of nitrogen compound and, where appropriate, 50 to 2,000 g/h of water in the form of steam. It is preferable for steam to be present, preferably in an amount from 200 to 1,000 g/h per liter of bulk volume of the catalyst.

The oxygen is preferably used diluted with inert gases, for example nitrogen and/or carbon dioxide. Oxygen is particularly preferably used in the form of air or air/nitrogen mixtures. The proportion by volume of inert gases can be, for example, up to 20 times the amount of oxygen. Amounts of inert gas of up to 10 times the proportion by volume of the amount of oxygen are preferred. It has also to be remembered that the amount of oxygen influences the temperatures occurring in the catalyst bed.

It is an essential feature of the process according to the invention that the gas mixture which is used contains nitrogen compounds in the form of inorganic and-/or organic amines and/or nitrogen oxides.

Processes for the reactivation of catalysts by the addition of aqueous ammonia have been disclosed (see, for example, U.S. Pat. Nos. 4,139,433, 4,107,031, and 4,432,953 and DE-OS (German Published Specification) No. 2,459,761. However, these processes are not suitable for the regeneration of catalysts with an elevated process temperature in the gas phase, since the ammonia treatment must take place in liquid, aqueous phase. Thus, these processes cannot be employed for the gas phase. Furthermore, any coke-like deposits which may be present on the catalyst cannot be removed with aqueous ammonia.

It is possible to use as inorganic amine according to the invention, for example, ammonia as such or, before its vaporization, in the form of aqueous solutions of any desired concentration. For example, such aqueous solutions may contain 1 to 40% by weight of ammonia.

Also suitable as inorganic amines are, for example, hydrazines and/or hydroxylamines. Ammonia is preferred. Examples of suitable organic amines are those having 1 to 6C atoms and 1 to 3N atoms, it being possible for the C:N atomic ratio to be 2:1 to 1:2, for example. Methylamine and 1,2-ethylenediamine are preferred for this. Examples of suitable nitrogen oxides are NO, $NO_2$, $N_2O$, $N_2O_2$, $N_2O_3$, $N_2O_4$ and $N_2O_5$, which can be in the form of single compounds or as mixtures with one another of any desired type. Nitrogen oxides can be used in the form of gases or in the form of aqueous solutions, of any desired concentration, for vaporization. Nitrogen oxides in which the nitrogen formally has the oxidation number $+1$, $+2$ or $+3$ are preferred.

It is also possible to use those nitrogen compounds which are converted, wholly or partially, into inorganic or organic amines or nitrogen oxides only under the conditions of the process according to the invention. Examples of nitrogen compounds of this type are substituted hydrazines, N- and/or O-substituted hydroxylamines, ureas, carboxamides, nitriles and semicarbazides, in each case preferably those having up to 4 carbon atoms and C:N atomic ratios of 2:1 to 1:2. It is also possible to use hydrates, carbonates, bicarbonates and other salt-like compounds of inorganic and organic amines in the regeneration process according to the invention.

Ammonia and 1,2-ethylenediamine are particularly preferably used as nitrogen compounds, ammonia being very particularly preferred.

Preferably, component (b) of the gas mixture is used in an amount of from 5 to 200 g/h per liter of bulk volume of the particular catalyst.

The individual components of the gas mixture to be employed according to the invention can be fed separately or together to the catalyst which is to be regenerated. Where ammonia or an organic amine is used as component (b), it is generally advantageous to introduce this component together with water and, for example, to vaporize together an aqueous ammonia or amine solution. Aqueous solutions of this type can contain, as long as the solubilities are appropriate, for example 1 to 50% by weight of ammonia or organic amine. Solutions of this type preferably have a minimum of 3% by weight and a maximum of the concentrations corresponding to saturation. It is possible in this manner also to introduce water into the process according to the invention, which then provides, wholly or partially, preferably wholly, the steam to be used where appropriate.

The process according to the invention can be carried out in the absence or in the presence of steam. It is preferably carried out in the presence of steam since, in general, more favorable results are then obtained, and there is then less elaboration involved in taking care of explosive limits.

The process according to the invention for catalyst regeneration can be carried out externally, that is to say with the catalyst removed into a special apparatus. In general in situ regeneration of the catalyst, which is likewise possible, is economically more advantageous, especially with regard to the saving of time and work. This entails the catalyst being regenerated in the reactor for amine production, without the catalyst being removed.

The catalyst regeneration according to the invention takes place at elevated temperature. This can be, for example, in the range from 200° to 600° C. The regeneration temperature is preferably suited to the fundamental process of amine production, namely in such a manner that the regeneration is carried out at the same temperature as the amine production or up to 80° C. above this, particularly preferably at up to 50° C. above this.

In a specific embodiment, the process according to the invention can be carried out as follows:

While maintaining the catalyst temperature, the supply of the nitroaromatic for the preparation of amine is stopped, and the reducing agent is replaced by a stream of nitrogen. Then, for example, a 5% strength aqueous solution of ammonia is fed in and vaporized. While gradually reducing the flow of nitrogen, air is correspondingly fed in at such a rate that the catalyst temperature becomes set at a maximum of 50° C. above the temperature of amine production. When no further temperature change is observed in the catalyst zone, or no further $CO_2$ is detectable in the exit gas, the regeneration is terminated after a further 0.1 to 5 hours where appropriate, for example by renewed replacement of the stream of air by a stream of nitrogen, termination of the feeding in of ammonia solution and, after sufficient interim flushing with nitrogen, renewed feeding in of the reducing gas, for example hydrogen or natural gas, and the nitroaromatic into the amine production.

It is not generally necessary to carry out a special reducing after-treatment of the regenerated catalyst. This applies, in particular, when, with introduction of the full amount of reducing gas for amine production, the aromatic nitro compound is brought to the desired target amount stepwise only over the course of, for example, 0.5 to 8 hours.

In general, the regeneration process according to the invention can be carried out under atmospheric pressure or the slightly increased pressure necessary to overcome the loss of pressure in the catalyst bed, or the pressure difference necessary to maintain a moving bed or fluidized bed. However, working under a reduced pressure, for example down to 0.1 bar, or under an increased pressure, for example up to 30 bar, is likewise possible. This may be advantageous if the process of amine production is not operated under atmospheric pressure, and the regeneration process is, for technical reasons, to be carried out under the same pressure as the amine production.

In a modified form of the regeneration process according to the invention, the latter can also be carried out on fresh catalysts as a preforming process. The procedure then corresponds to that described above, but the treatment with the regenerating gas which contains the components (a) and (b) and, where appropriate, (c) generally takes less time, but it should last at least 3 hours in general.

The advantages of the regeneration process according to the invention are, on the one hand, the possibility of being able to regenerate in situ and, on the other hand, the striking prolongation of the cycles between individual regenerations. It is particularly surprising that these advantages, which are of economic importance for amine production, can be achieved by the very straightforward measures, which are easy to put into industrial practice, of the regeneration process according to the invention.

The examples which follow illustrate the process according to the invention without restricting it in any way to these embodiments.

EXAMPLES

Catalysts used

Catalyst A

This catalyst was prepared in accordance with Example 1 of DE-OS (German Published Specification) 2,849,002 and contained 6 g of palladium, 9 g of vanadium and 6 g of lead per liter of aluminium oxide support. This catalyst was used in Examples 1, 2 and 11.

Catalyst B

Commercially available copper chromite catalyst (Ventron 11845, Alfa catalogue 1984, European edition, page 165). According to the statement in the catalogue the characteristic content of the catalyst is 42% by weight of CuO and 38% by weight of $Cr_2O_3$. A Debye-Scherrer X-ray picture showed that the catalyst consists predominantly of copper-(II)-chromite ($CuCr_2O_4$). This catalyst was used in Examples 3 to 10.

Comments on Examples 1, 2 and 11

Examples 1, 2 and 11 were carried out in a cage reactor which was operated as a differential hydrogenation reactor and had a total volume of 300 ml under atmospheric pressure. Reactors of this type are especially suitable for kinetic investigations and are described in detail by, for example, A. Schulz-Walz, D. C. Hempel, Z. Kricsfalussy and C. Rasp in Chem. Ing. Technik, 53, (8), 637–640 (1981). The reactor was charged with 50 ml of catalyst A. The liquids were fed in using a minimetering pump, vaporized upstream of the reactor in a preheater at 300° C. and passed together with the feed gas streams into the reactor. The gaseous exit stream was passed successively through a cold trap cooled with ice and one cooled with solid $CO_2$, in order to extract condensable reaction products. The condensates were combined at intervals of 8 hours and quantitatively analysed by gas chromatography.

The increase in the reaction temperature compared with the examples in DE-OS (German Published Specification) No. 2,849,002 is intentional in order to be able to investigate the deactivation of the catalyst, which normally extends over a period of 900 to 1,500 hours, with a time-compression effect. Because of the increased reaction temperature, the aniline selectivities in these examples are also lower than would be possible under optimum reaction conditions for the preparation of aniline.

EXAMPLE 1

(for comparison)

Feedstocks 50 ml of fresh catalyst A
20 ml/h nitrobenzene (0.195 mol/h)
25 l/h hydrogen (1.040 mol/h)
1.5 l/h nitrogen (0.062 mol/h)
Reaction conditions:
Catalyst temperature: 420° C.
Pressure: 1 bar The conversion of nitrobenzene after a reaction time of 8 hours was 91%, and the selectivity of aniline formation, based on reacted nitrobenzene, was 92%. The conversion of nitrobenzene decreased to 61% over the course of 200 hours, and the selectivity of aniline formation, based on reacted nitrobenzene, decreased to 66%.

After 200 hours of operation, the catalyst was regenerated as follows:

The feeding in of nitrobenzene and the feeding in of hydrogen were stopped, and 12.5 g/h steam were generated using the preheater operated at 300° C., and this was passed into the reactor together with 16 l/h nitrogen. Air was metered in stepwise, and the feeding in of nitrogen was correspondingly reduced until a figure of 8 l/h nitrogen and 8 l/h air was reached. The metering in of air was carried out while monitoring the catalyst temperature so that 450° C. was not exceeded. Regeneration was continued with the air/nitrogen/steam mixture until $CO_2$ was no longer detectable in the exit stream by IR spectroscopy, which took 13 hours.

Then an interim flushing with nitrogen was carried out, the feeding in of water was stopped, and the original catalyst temperature and the $N_2/H_2$ stream were restored. The feeding in of nitrobenzene was brought to the original target amount within 30 minutes, and thus the preparation of aniline was resumed. The conversion of nitrobenzene after a further 8 hours was 92%, and the selectivity of aniline formation, based on reacted nitrobenzene, was 89%.

The conversion of nitrobenzene decreased to 37% over the course of a further 72 hours, and the selectivity of aniline formation, based on reacted nitrobenzene, decreased to 17%.

EXAMPLE 2

(according to the invention)

The process was carried out with fresh catalyst A as in Example 1. The conversion of nitrobenzene after a reaction time of 8 hours was 91%, and the selectivity of aniline formation, based on reacted nitrobenzene, was likewise 91%. The conversion of nitrobenzene decreased to 62% over the course of 200 hours, and the selectivity of aniline formation decreased to 68%.

The catalyst was then regenerated under conditions as indicated in Example 1, but 12.5 g/h of a 5% strength aqueous ammonia solution was used in place of 12.5 g/h steam.

The preparation of aniline was then continued as described in Example 1.

The conversion of nitrobenzene 8 hours after the end of the regeneration (=after the start of the renewed feeding in of the target amount of nitrobenzene) was 90%, and the selectivity of aniline formation, based on reacted nitrobenzene, was 88%. There were only inconsiderable changes in these figures over the course of a further 200 hours. The conversion of nitrobenzene was then 88%, and the selectivity of aniline formation, based on reacted nitrobenzene, was 90%.

EXAMPLES 3 TO 10

Examples 3 to 6 and Example 8 are comparison examples, while Examples 7, 9 and 10 are examples according to the invention which demonstrate the favourable effect of the process according to the invention on the preparation of aniline from nitrobenzene using natural gas and steam on a copper chromite catalyst according to EP-OS (European Published Specification) No. 0,087,690.

The tube reactor used corresponded to the reactor of Example 15 of EP-OS (European Published Specification) No. 0.087,690. A difference from the process described there was that the preparation of aniline was carried out under increased pressure and using recycled gas, that is to say the gaseous components which were not condensed by cooling water were returned to the reactor inlet using a recycling gas blower. The amounts fed in and the reactor conditions for the preparation of aniline are shown in foot-note 1 to Table 1.

The regenerations were carried out as follows:

The procedure corresponded to Example 1. The amounts fed in were as follows, in accordance with the larger bulk volume of catalyst:

At the start of the regeneration: 350 l/h nitrogen.

During the regeneration: 175 l/h nitrogen and 175 l/h air and 550 g/h water (for Examples 3 to 6 and 8), 550 g/h 5% strength aqueous ammonia solution (for Examples 7 and 9) and 550 g/h 5% strength aqueous solution of 1,2-ethylenediamine (for Example 10).

The results for Examples 3 to 10 are compiled in Table 1. The selectivity of aniline formation in these examples was 95±1 mol % based on reacted nitrobenzene. The decrease in conversion over the duration of the cycle is approximately linear. At the start of Example 6, the copper chromite catalyst had been operated for 7,500 hours for aniline production in accordance with EP-OS (European Published Specification) No. 0,087,690. At this time, the duration of the cycle had already decreased to 168 hours from the original approximately 300 hours. Examples 7, 9 and 10 according to the invention show that it is possible, using the regeneration according to the invention, to return to a duration of the cycle which is of the original order of magnitude.

TABLE 1

| Example No.[1] | Production cycle No. | Nitrobenzene conversion[2] [%] Start | Finish | Duration of cycle [h] | Regeneration before the cycle |
|---|---|---|---|---|---|
| 3 | 1 | 96 | 62 | 240 | without $NH_3$ |
| 4 | 2 | 93 | 66 | 264 | without $NH_3$ |
| 5 | 3 | 95 | 65 | 312 | without $NH_3$ |
| 6 | 40 | 92 | 50 | 168 | without $NH_3$ |
| 7 | 41 | 95 | 67 | 304 | with $NH_3$ |
| 8 | 42 | 95 | 63 | 210 | without $NH_3$ |
| 9 | 43 | 96 | 65 | 304 | with $NH_3$ |
| 10 | 44 | 95 | 65 | 304 | with $H_2N-CH_2CH_2-NH_2$ |

[1]Amounts fed in:
550 g/h nitrobenzene
550 g/h water
260 l/h natural gas (liters at STP)
Reaction conditions:
4 bar pressure
420° C. maximum catalyst temperature
300 l/h recycled gas (effective liters)
[2]Nitrobenzene conversion at the start and at the finish of the particular production cycle.

EXAMPLE 11

(according to the invention)

The process was carried out as described in Example 1 with fresh catalyst A. The conversion of nitrobenzene after a reaction time of 8 hours was 91.5%, and the selectivity of aniline formation, based on reacted nitrobenzene, was 91%. The conversion of nitrobenzene decreased to 63% over the course of 200 hours, and the selectivity of aniline formation decreased to 66%.

Then regeneration was carried out as indicated in Example 1, but 1.1 g/h nitrogen monoxide (NO) was added to the regenerating gas. The preparation of aniline was then continued as described in Example 1.

The conversion of nitrobenzene 8 hours after completion of the regeneration (=after the start of renewed feeding in of the target amount of nitrobenzene) was 91%, and the selectivity of aniline formation, based on reacted nitrobenzene, was 92%. The conversion of nitrobenzene decreased over the course of a further 144 hours to 56%, and the selectivity of aniline formation, based on reacted nitrobenzene, decreased to 65%.

EXAMPLE 12

(according to the invention)

A single-tube hydrogenation reactor (tube diameter 32 mm, tube length 1300 mm) was packed with one liter of a catalyst which contained 9 g of palladium, 9 g of vanadium and 3 g of lead per liter of aluminium oxide support (prepared in accordance with catalyst A, see introduction to the example section). The reaction temperature was maintained at 260° to 280° C. by a boiling heat-transfer oil. Nitrobenzene was vaporized at 160° to 180° C. in the stream of hydrogen, and was passed through the reactor from the bottom to the top. The loading was 0.6 kg of nitrobenzene/h.1 of catalyst at 6 mol of $H_2$ per mol of nitrobenzene. The gaseous reaction product was condensed and examined by gas chromatography. The nitrobenzene conversion was 100%, and the aniline selectivity was 100–99.5%. The test was stopped after the nitrobenzene conversion fell to 99.5%. The life was 1,690 hours. The subsequent regeneration was carried out in such a manner that nitrogen, air and aqueous ammonia solution were passed in simultaneously through the nitrobenzene vaporizer until $CO_2$ was no longer detectable at the exit.

Amounts fed in:
  200 l of nitrogen per hour
  200 l of air per hour
  200 ml of 25% strength aqueous ammonia Solution per hour
Regeneration time:
  4 hours After this regeneration, the catalyst was again used for the hydrogenation of nitrobenzene. The test conditions were the same as described above. The nitrobenzene conversion was again 100%, and the aniline selectivity was again 99.0–99.5%. This production cycle reached a life (=decrease of the nitrobenzene conversion to 99.5%) of 2,940 hours.

EXAMPLE 13

(for comparison)

The process was carried out exactly as in Example 12 but the regeneration after 1,650 hours was carried out without addition of an aqueous ammonia solution. The life reached by the catalyst in the subsequent production cycle was 1,820 hours (until the nitrobenzene conversion fell to 99.5%).

EXAMPLE 14

(according to the invention)

The process was carried out as in Example 12, but in place of nitrobenzene a corresponding amount of o-nitrotoluene was passed in, and this was reduced to o-toluidine. The conversions and selectivities were initially as indicated in Example 12. The o-nitrotoluene conversion had decreased to 99.5% after 520 hours. Regeneration was carried out as indicated in Example 12. Following the regeneration, it took 795 hours until the o-nitrotoluene conversion had again fallen to 99.5%.

EXAMPLE 15

(for comparison)

The process was carried out as in Example 14, but the regeneration after 550 hours was carried out without addition of an aqueous ammonia solution. The life reached by the catalyst in the subsequent production cycle was only 515 hours (until the o-nitrotoluene conversion fell to 99.5%).

EXAMPLE 16

(according to the invention)

The process was carried out as in Examples 12 and 14, but a corresponding amount of p-nitrotoluene was passed in, and this was reduced to p-toluidine. The conversions and selectivities are initially as indicated in Example 12. The p-nitrotoluene conversion had decreased to 99.5% after 730 hours. Regeneration was carried out as indicated in Example 12. Following the regeneration, it took 1,045 hours until the p-nitrotoluene conversion had again fallen to 99.5%.

EXAMPLE 17

(for comparison)

The process was carried out as in Example 16, but the regeneration after 690 hours was carried out without addition of an aqueous ammonia solution. The life reached by the catalyst in the subsequent reaction cycle was only 715 hours (until the p-nitrotoluene conversion fell to 99.5%).

EXAMPLE 18

(according to the invention)

The process was carried out as in Examples 12 and 14, but a corresponding amount of m-nitrotoluene was passed in, and this was reduced to m-toluidine. The conversions and selectivities were initially as indicated in Example 12. The m-nitrotoluene conversion had decreased to 99.5% after 605 hours. Regeneration was carried out as indicated in Example 12. Following the regeneration, it took 940 hours until the m-nitrotoluene conversion had again fallen to 99.5%.

EXAMPLE 19

(for comparison)

The process was carried out as in Example 18, but the regeneration after 690 hours was carried out without addition of an aqueous ammonia solution. The life reached by the catalyst in the subsequent production cycle was only 630 hours (until the m-nitrotoluene conversion fell to 99.5%).

It will be appreciated that the instant specification and claims are set forth by way of illustration and not limitation, and that various modifications and changes may be made without departing from the spirit and scope of the present invention.

What is claimed is:

1. A process for the regeneration of a catalyst for the gas-phase reduction of aromatic nitro compounds to aromatic amines comprising treating the catalyst in a catalyst zone at a temperature of 200° C. to 600° C., wherein the catalyst contains a metal selected from the group consisting of copper, iron, nickel, palladium, platinum and mixtures thereof, said metal being in metallic form or in the form of compounds, with a gas mixture which contains (a) oxygen and (b) a nitrogen compound selected from the group consisting of inorganic amines, organic amines and nitrogen oxides, said regeneration being conducted until no temperature change is observed in the catalyst zone, or until no $CO_2$ is detectable in gas exiting said zone and at a pressure of 0.1 to 30 bars, wherein the oxygen is fed at a rate of 5 to 100 l/h and the nitrogen compound is fed at a rate of 2 to 1,000 g/h per liter of bulk volume of the catalyst.

2. A process according to claim 1 wherein the gas mixture further comprises steam.

3. A process according to claim 1, wherein the catalyst is a catalyst which has been used for the preparation of aniline form nitrobenzene.

4. A process according to claim 1, which further comprises terminating the regeneration after a further 0.1 to 5 hours.

5. A process according to claim 1, wherein said metal is modified by other metals or metal compounds.

6. A process according to claim 5, wherein said other metal is chromite.

7. A process according to claim 1, wherein the nitrogen compound is fed at a rate of 5 to 200 g/h per liter of bulk volume of catalyst.

8. A process according to claim 2, wherein the steam is fed at a rate of 50 to 2,000 g/h per liter of bulk volume of the catalyst.

9. A process according to claim 2, wherein the steam is fed at a rate of 200 to 1,000 g/h per liter of bulk volume of the catalyst.

10. A process according to claim 1, wherein the nitrogen compound is selected from the group consisting of ammonia, hydrazines, hydroxylamines, organic amines having 1 to 6C atoms and 1 to 3N atoms, NO, $NO_2$, $N_2O$, $N_2O_2$, $N_2O_3$, $N_2O_4$, $N_2O_5$ and mixtures thereof.

11. A process according to claim 1, wherein the nitrogen composed is selected from the group consisting of ammonia, 1,2-ethylenediamine and mixtures thereof.

12. A process according to claim 1, wherein the nitrogen compound before its vaporization comprises an aqueous solution of ammonia containing 1 to 40% by weight of ammonia.

13. A process according to claim 1, wherein the treatment with the gas mixture is carried out at the same temperature as the gas phase reduction of aromatic nitro compounds to aromatic amines or up to 80° C. above the temperature.

14. A process according to claim 1, wherein the oxygen is diluted with one or more inert gases.

15. A process according to claim 14, wherein the proportion by volume of the inert gases is up to 20 times the amount of the oxygen.

16. A process according to claim 14, wherein the proportion by volume of the inert gases is up to 10 times the amount of the oxygen.

* * * * *

UNITED STATES PATENT AND TRADEMARK OFFICE
CERTIFICATE OF CORRECTION

PATENT NO. : 4,714,689

DATED : December 22, 1987

INVENTOR(S) : Günter Stammann, et al.

It is certified that error appears in the above-identified patent and that said Letters Patent is hereby corrected as shown below:

| | |
|---|---|
| Title Page, Abstract, lines 5-6 | Correct spelling of --appropriate-- |
| Col. 1, lines 38, 41 | Delete "stream" and substitute --steam-- |
| Col. 1, line 52 | Delete "regenerating" and substitute --regeneration--. |
| Col. 2, line 30 | Delete "ised" and substitute --used-- |
| Col. 10, line 19 | Delete "are" and substitute --were-- |
| Col. 11, line 7 | Before "$CO_2$" insert --further-- |
| Col. 11, line 16 | Delete "form" and substitute --from-- |
| Col. 11, line 23 | After "metal" insert --further-- |

Signed and Sealed this

Second Day of August, 1988

Attest:

DONALD J. QUIGG

*Attesting Officer*           *Commissioner of Patents and Trademarks*

UNITED STATES PATENT AND TRADEMARK OFFICE
CERTIFICATE OF CORRECTION

PATENT NO. : 4,714,689

DATED : December 22, 1987

INVENTOR(S) : Günter Stammann, et al.

It is certified that error appears in the above-identified patent and that said Letters Patent is hereby corrected as shown below:

Col. 11, line 23            After "metal is" insert --chromium in the form of--

Signed and Sealed this

Sixth Day of September, 1988

Attest:

DONALD J. QUIGG

Attesting Officer           Commissioner of Patents and Trademarks